United States Patent [19]
Lockhart et al.

[11] Patent Number: 6,033,860
[45] Date of Patent: Mar. 7, 2000

[54] EXPRESSION PROFILES IN ADULT AND FETAL ORGANS

[75] Inventors: David J. Lockhart; Janet A. Warrington, both of Mountain View; Archana Nair, Santa Clara, all of Calif.

[73] Assignee: Affymetrix, Inc., Santa Clara, Calif.

[21] Appl. No.: 09/182,991

[22] Filed: Oct. 30, 1998

Related U.S. Application Data

[60] Provisional application No. 60/063,857, Oct. 31, 1997.

[51] Int. Cl.$^7$ ........................................ C12Q 1/68
[52] U.S. Cl. ............................. 435/6; 536/24.31
[58] Field of Search ............................. 435/6; 536/24.31

[56] References Cited

U.S. PATENT DOCUMENTS

| | | | |
|---|---|---|---|
| 5,569,588 | 10/1996 | Ashby et al. | 435/6 |
| 5,700,637 | 12/1997 | Southern | 435/6 |

FOREIGN PATENT DOCUMENTS

| | | |
|---|---|---|
| 0 717 105 | 6/1996 | European Pat. Off. . |
| 8-009969 | 5/1996 | Japan . |
| 89/10977 | 11/1989 | WIPO . |
| 94/26905 | 11/1994 | WIPO . |
| 95/13374 | 5/1995 | WIPO . |
| 97/27317 | 7/1997 | WIPO . |

OTHER PUBLICATIONS

Zhao et al. "High–Density cDNA Filter Analysis: Novel Approach for Large–Scale, Quantitative Analysis of Gene expression" Gene, vol. 156, 1995, pp. 207–213.

Takahashi et al. "High–Density cDNA Analysis of the Expression Profiles of the Genes Preferentially Expressed in Human Brain" Gene, vol. 164, 1995, pp. 219–227.

Schena et al. "Parallel Human Genome Analysis: Microarray–Based Expression Monitoring of 1000 Genes" Proceedings of the National Academy of Sciences of USA, vol. 93, No. 20, Oct. 1996, pp. 10614–10619.

S. Borman "DNA Chips come of Age after Period of Gestation, Technology for Genetic Analysis in Blossoming" Chemical and Engineering News, vol. 74, No. 50, Dec. 9, 1996, pp. 42/43.

Lockhart et al. "Expression Monitoring by Hybridization to High–Density Oligonucleotide Arrays" Nature Biotechnology, vol. 14, Dec. 1996, pp. 1675–1680.

Schena et al. "Quantitative Monitoring of Gene Expression Patterns with a Complementary DNA Microarray" Science, vol. 270, No. 5235, Oct. 20, 1995.

Kauppinen et al. "Contribution of Cytoplasmic Polypeptides to the Proton NMR Spectrum of Developing Rat Cerebral Cortex" Magn. Reson. Med., vol. 25, No. 2, 1992, pp. 398–407.

B.J. Sedlak, "Gene Chip Technology Ready to Impact Diagnostic Markets" Genetic Engineering News, Dec. 1997, pp. 1, 14, 34.

*Primary Examiner*—James Ketter
*Attorney, Agent, or Firm*—Banner & Witcoff, Ltd.

[57] ABSTRACT

Expression profiles have been constructed for liver and brain, in adult and fetal and adolescent tissue. These provide the art with probes which are highly differentially expressed among stages and organs. The profiles and probes can be used to prioritize potential drug targets, to monitor disease progression and remission, and to assess drug metabolism. Solid supports are also provided which facilitate these uses.

22 Claims, 1 Drawing Sheet

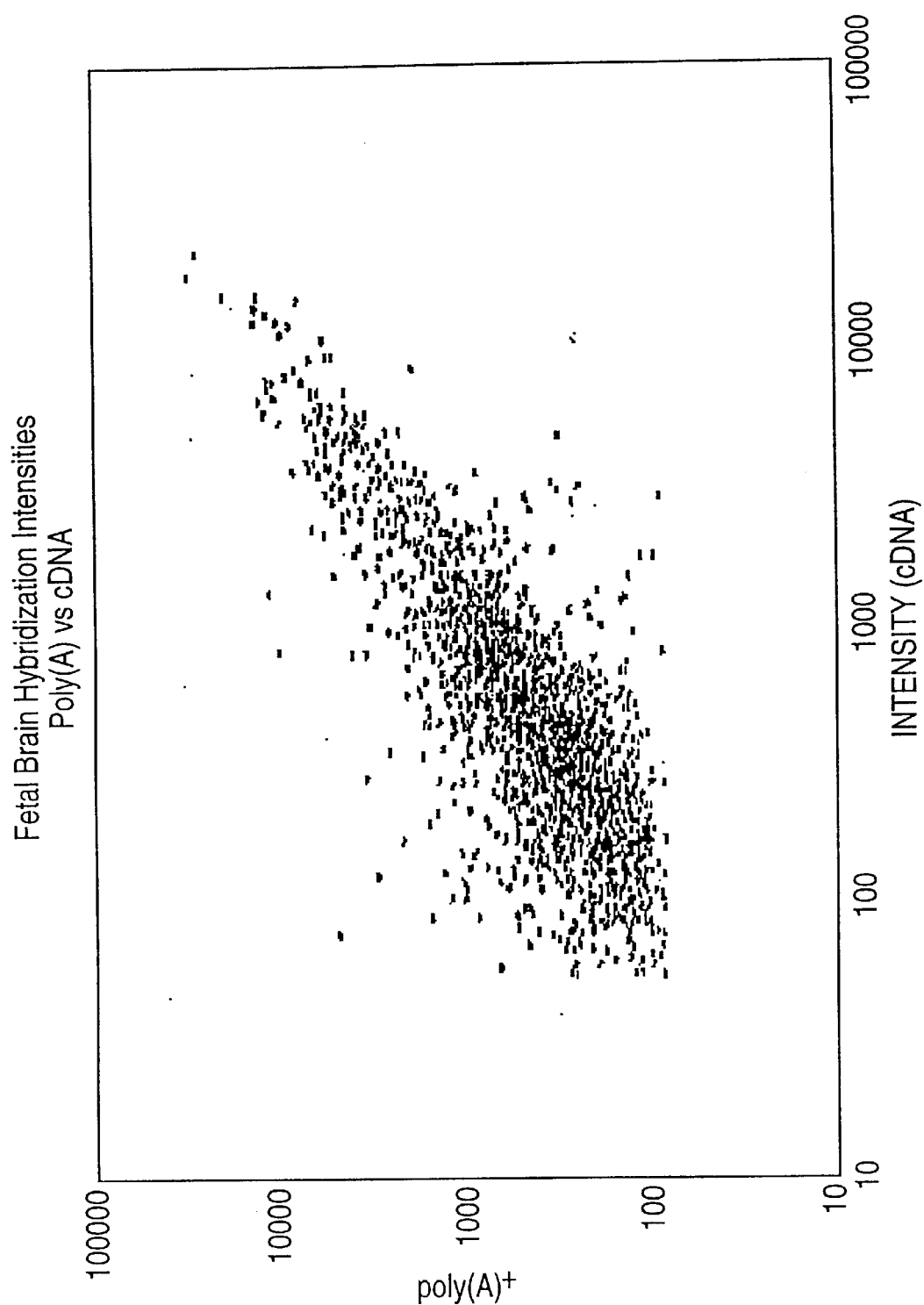

EXPRESSION PROFILES IN ADULT AND FETAL ORGANS

This application claims benefit of Provisional Application Ser. No. 60/063,857 filed Oct. 31, 1997.

BACKGROUND OF THE INVENTION

Expression profiles of genes in particular organs or disease states or developmental stages provide molecular tools for evaluating toxicity, drug efficacy, drug metabolism, development, and disease monitoring. Changes in the expression profile from a baseline profile can be used as an indication of such effects.

SUMMARY OF THE INVENTION

It is an object of the present invention to provide a method of screening a drug for deleterious side effects on a cell.

It is another object of the present invention to provide a method of distinguishing between a fetal and an adult liver sample.

It is an object of the present invention to provide a method of distinguishing between a fetal and adult brain tissue.

Another object of the invention is to provide a method of determining the source of a tissue as adult brain or adult liver.

Another object of the invention is to provide a method of distinguishing a tissue source as fetal brain or fetal liver.

Another object of the invention is to provide a solid support for screening a drug for deleterious side effects on a cell.

Another object of the invention is to provide a solid support for distinguishing between a fetal and an adult liver sample.

Still another object of the invention is to provide a solid support for distinguishing between a fetal and adult brain tissue.

Yet another object of the invention is to provide a solid support for determining the source of a tissue as adult brain or adult liver.

Another object of the invention is to provide a solid support for distinguishing a tissue source as fetal brain or fetal liver.

These and other objects of the invention are achieved by providing a method of screening a drug for deleterious side effects on a cell. The method comprises the step of:

assaying for the amount of expression in the cell of two or more genes selected from the group consisting of: G6PD, calcium channel, synaptotagamin, neuromodulin, calmodulin, nicotinic acetylcholine receptor beta 2, VLDLR, udulin1/undulin/extracellular matrix glycoprotein, pyruvate dehydrogenase E1, apolipoprotein B100, hepatocyte gf, IGF binding protein 1, ubiquitin, bone morphogenetic protein precursor, cytochrome p450-2E1, and thymosin beta-10, wherein the expression in the cell is assayed before and after the cell has been contacted with the drug, wherein alteration of the amount of expression of at least one of these genes by the drug is indicative of a deleterious side effect.

According to another embodiment of the invention a method of distinguishing between a fetal and an adult liver sample is provided. The method comprises the step of:

assaying for expression in the sample of two or more genes selected from the group consisting of: G6PD, calmodulin, VLDLR, udulin1/undulin/extracellular matrix glycoprotein, hepatocyte gf, IGF binding protein 1, ubiquitin, cytochrome p450-2E1, and thymosin beta-10, wherein expression of G6PD, VLDLR, udulin1/undulin/extracellular matrix glycoprotein, cytochrome p450-2E1, and thymosin beta-10 are indicative of an adult liver, and expression of calmodulin, hepatocyte gf, IGF binding protein 1, and ubiquitin are indicative of a fetal liver.

According to still another embodiment of the invention a method of distinguishing between a fetal and adult brain tissue is provided. The method comprises the step of:

assaying for expression in the tissue of two or more genes selected from the group consisting of: nicotinic acetylcholine receptor beta 2, ubiquitin, and thymosin beta-10, wherein expression of nicotinic acetylcholine receptor beta 2 or ubiquitin indicates an adult brain.

Another aspect of the invention is a method of determining the source of a tissue as adult brain or adult liver. The method comprises the steps of:

assaying for expression in the tissue of two or more genes selected from the group consisting of: calcium channel, synaptotagamin, neuromodulin, calmodulin, nicotinic acetylcholine receptor beta 2, VLDLR, udulin1/undulin/extracellular matrix glycoprotein, pyruvate dehydrogenase E1, apolipoprotein B100, hepatocyte gf, IGF binding protein 1, ubiquitin, bone morphogenetic protein precursor, and cytochrome p450-2E1, wherein expression of calcium channel, synaptotagamin, neuromodulin, calmodulin, nicotinic acetylcholine receptor beta 2, ubiquitin, or bone morphogenetic protein precursor indicates a brain source for the tissue and wherein expression of pyruvate dehydrogenase E1, VLDLR, udulin1/undulin/extracellular matrix glycoprotein, apolipoprotein B100, thymosin beta-10, hepatocyte gf, IGF binding protein 1, or cytochrome p450-E1 indicates a liver source for the tissue.

Still another aspect of the invention is a method of distinguishing a tissue source as fetal brain or fetal liver. The method comprises the step of:

assaying for expression in the tissue of two or more genes selected from the group consisting of: G6PD, calcium channel, synaptotagamin, neuromodulin, pyruvate dehydrogenase E1, apolipoprotein B100, hepatocyte gf, IGF binding protein 1, ubiquitin, bone morphogenetic protein precursor, and thymosin beta-10, wherein expression of G6PD, calcium channel, synaptotagamin, neuromodulin, thymosin beta-10 or bone morphogenetic protein precursor indicates a fetal brain source and expression of pyruvate dehydrogenase E1, apolipoprotein B100, hepatocyte gf, IGF binding protein 1, ubiquitin, indicates a fetal liver source.

Another embodiment of the invention provides a solid support for screening a drug for deleterious side effects on a cell. The solid support comprises: at least two oligonucleotides for probing two or more genes selected from the group consisting of: G6PD, calcium channel, synaptotagamin, neuromodulin, calmodulin, nicotinic acetylcholine receptor beta 2, VLDLR, udulin1/undulin/extracellular matrix glycoprotein, pyruvate dehydrogenase E1, apolipoprotein B100, hepatocyte gf, IGF binding protein 1, ubiquitin, bone morphogenetic protein precursor, cytochrome p450-2E1, and thymosin beta-10, wherein each oligonucleotide comprises a sequence which is complementary to one of the two or more genes.

Yet another aspect of the invention is a solid support for distinguishing between a fetal and an adult liver sample. The solid support comprises: two or more oligonucleotides for detecting two or more genes selected from the group consisting of: G6PD, calmodulin, VLDLR, udulin1/undulin/extracellular matrix glycoprotein, hepatocyte gf, IGF binding protein 1, ubiquitin, cytochrome p450-2E1, and thymosin beta-10 wherein each oligonucleotide comprises a sequence which is complementary to one of the two or more genes.

In mother aspect of the invention a solid support for distinguishing between a fetal and adult brain tissue is provided. The solid support comprises: two more oligonucleotides for detecting two or more genes selected from the group consisting of: nicotinic acetylcholine receptor beta 2, ubiquitin, and thymosin beta-10, wherein each oligonucleotide comprises a sequence which is complementary to one of the two or more genes.

In sill another aspect of the invention a solid support for determining the source of a tissue as adult brain or adult liver is provided. The solid support comprises:

two or more oligonucleotides for detecting two or more genes selected from the group consisting of: calcium channel, synaptotagamin, neuromodulin, calmodulin, nicotinic acetylcholine receptor beta 2, VLDLR, udulin1/undulin/extracellular matrix glycoprotcin, pyruvate dehydrogenase E1, apolipoprotein B100, hepatocyte gf, IGF binding protein 1, ubiquitin, bone morphogenetic protein precursor, and cytochrome p450-2E1, wherein each oligonucleotide comprises a sequence which is complementary to one of the two or more genes Another embodiment of the invention is a solid support for distinguishing a tissue source as fetal brain or fetal liver. The solid support comprises: two or more oligonucleotides for detecting two or more genes selected from the group consisting of: G6PD, calcium channel, synaptotagamin, neuromodulin, pyruvate dehydrogenase E1, apolipoprotein B100, hepatocyte gf, IGF binding protein 1, ubiquitin, bone morphogenetic protein precursor, and thymosin beta-10, wherein each oligonucleotide comprises a sequence which is complementary to one of the two or more genes.

BRIEF DESCRIPTION OF THE DRAWINGS

FIG. 1 shows a plot of the fetal brain hybridization intensities, poly(A)$^+$ versus cDNA yielded a line with a slope of 1.

DETAILED DESCRIPTION

Genes have been found whose expression is varied greatly ($\geq$10 fold) between different developmental stages and between different organs in the same developmental stages. Thus these genes can be used as interrogators (probes) to determine the expression pattern of unknown cells or samples to identify them as belonging to the appropriate developmental stage or organ source. The genes are listed in Table 4. The complete sequences of the genes are available from GenBank using the accession numbers shown in the table Any selection of at least 2 through 16 of the genes can be used as interrogators. For a particular interrogation of two conditions or sources, it is desirable to select those genes which display a great deal of difference in the expression pattern between the two conditions or sources. At least a two-fold difference is desirable, but a five-fold or ten-fold difference is preferred.

Interrogations of the genes or proteins can be performed to yield different information. Potential drugs can be screened to determine if the expression of these genes is inappropriately altered. This may be useful, for example, in determining whether a particular drug is prescribed to a pregnant woman. In the case where a fetally expressed gene's expression is affected by the potential drug, prohibition of the drug to pregnant woman is indicated. Similarly, a drug which causes expression of a gene which is not normally expressed by a fetus, should be prohibited to pregnant woman.

Molecular expression markers for either brain or liver can be used to confirm tissue source identifications made on the basis of morphological criteria. In some situations, identifications of cell type or source is ambiguous based on classical criteria In these situations the molecular expression markers of the present invention are useful.

In addition, disease progression involving either the brain or the liver can be monitored by following the expression patterns of the involved organs using the molecular expression markers of the present invention Perturbed expression can be observed in the diseased state. Monitoring of the efficacy of certain drug regimens can also be accomplished by following the expression patterns of the molecular expression markers.

Although only a few different developmental time points have been observed, as shown in the examples below, other developmental stages can be studied using these same molecular expression markers. The importance of these markers in development has been shown here, however, variations in their expression may occur at other times. For example, one could study the expression of these markers at other gestational stages, at birth, postnatally, and throughout the human life cycle.

Solid supports containing oligonucleotide probes for differentially expressed genes can be filters, polyvinyl chloride dishes, etc. Any solid surface to which oligonucleotides can be bound, either directly or indirectly, either covalently or non-covalently, can be used. A preferred solid support is a high density array or DNA chip. These contain a particular oligonucleotide probe in a predetermined location on the array. Each predetermined location may contain more than one molecule of the probe, but each molecule within the predetermined location has an identical sequence. Such predetermined locations are termed features. There may be, for example, from 2, 10, 100, 1000, to 10,000, 100,000, or 400,000 of such features on a single solid support. The solid support, or the area within which the probes are attached may be on the order of a square centimeter.

Oligonucleotide probe arrays for expression monitoring can be made and used according to any techniques known in the art. See for example, Lockhart, D. J. et al., *Nature Biotechnology* 14:1675–1680 (1996) and McGall, G. et al., *Proc. Nat.Acad.Sci. USA* 93:13555–13460 (1996).

The genes which are assayed or interrogated according to the present invention are typically in the form of mRNA or reverse transcribed mRNA. The genes may be cloned or not. The genes may be amplified or not. The cloning itself does not appear to bias the representation of genes within a population. However, it may be preferable to use polyA+ RNA as a source, as it can be used with less processing steps. The sequences of the expression marker genes are in the public databases. Table 4 provides the accession numbers for the sequences. The sequences of the genes in GenBank are expressly incorporated herein. Some of the genes are also the subject of scientific and learned journal articles. These include: Anand, R. and Lindstrom, J., Nucleotide sequence of the human nicotinic acetylcholine receptor beta 2 subunit gene, Nucleic Acids Res. 18 (14), 4272 (1990) (MEDLINE 90332444); Takizawa, T., Huang, I. Y., Ikuta, T. and Yoshida, A., Human glucose-6-phosphate dehydrogenase: primary structure and cDNA cloning, Proc. Natl. Acad. Sci. U.S.A. 83 (12), 4157–4161 (1986) (MEDLINE 86233391); Karathanasis, S. K., Apolipoprotein multigene family: tandem organization of human apolipoprotein Al, CIII, and AIV genes, Proc. Natl. Acad. Sci. U.S.A. 82 (19), 6374–6378 (1985) (MEDLINE 86016704); Sakai, J., Hoshino, A., Takahashi, S., Miura, Y., Ishii, H., Suzuki, H., Kawarabayasi, Y. and Yamamoto, T., Structure, chromosome location, and expression of the human very low density lipoprotein receptor gene, J. Biol. Chem. 269 (3), 2173–2182 (1994) (MEDLINE 94124575); Schuppan, D., Cantaluppi, M., Becker, J., Veit, A., Bunte, T., Troyer, D., Schuppan, F., Schmid, M., Ackermann, R. and Hahn, E., Undulin, an Extracellular Matrix Glycoprotein Associated with Collagen Fibrils, J. Biol. Chem. 265, 8823–8832 (1990) (MEDLINE 90256812); Just, M., Herbst, H., Hummel, M., Durkop, H., Tripier, D., Stein, H. and Schuppan, D., Undulin is a novel member of the fibronectin-tenascin family of extracellular matrix glycoproteins, J. Biol. Chem. 266, 17326–17332 (1991)(MEDLINE 91373351); Ehrenborg, E., Larsson, C., Stern, I., Janson, M., Powell, D. R. and Luthman, H., Contiguous localization of the genes encoding human insulin-like growth factor binding proteins 1 (IGBP1) and 3 (IGBP3) on chromosome 7, Genomics 12 (3), 497–502 (1992) (MEDLINE 92217971); Kosik, K. S., Orecchio, L. D., Bruns, G. A., Benowitz, L. I., MacDonald, G. P., Cox, D. R. and Neve, R. L., Human GAP-43: its deduced amino acid sequence and chromosomal localization in mouse and human, Neuron 1 (2), 127–132 (1988)(MEDLINE 90166498; Perin, M. S., Johnston, P. A., Ozcelik, T., Jahn, R., Francke, U. and Sudhof, T. C., Structural and functional conservation of synaptotagmin (p65) in Drosophila and humans, J. Biol. Chem. 266 (1), 615–622 (1991) (MEDLINE 91093190); Fischer, R., Koller, M., Flura, M., Mathews, S., Strehler-Page, M. A., Krebs, J., Penniston, J. T., Carafoli, E. and Strehler, E. E,. Multiple divergent mRNAs code for a single human calmodulin, J. Biol. Chem. 263 (32), 17055–17062 (1988)(MEDLINE 89034207). Each of these articles is also expressly incorporated herein.

Glucose-6-phosphate dehydrogenase deficiency can lead to significant hemolysis. Hemolytic crisis can be induced by exposure to an oxidant, producing profound drops in hematocrit and hemoglobin levels. Calmodulin is a calcium binding protein which controls the assembly of myosin molecules. Calcium channel is involved in ischemic heart disease, stroke and neuronal development and transmission. Neuromodulin is also known as GAP-43. It is involved in neuronal development. Prooncoprotein EWS binds to neuromodulin. VLDLR is the very low density lipoprotein receptor. It is involved in hyper-cholesterolemia. Undulin is involved with kidney diseases, kidney transplantation and hemodialysis. (Clin Nephrol 44(3), 178–184 (1995)). It is also involved in schistosomiasis and alcoholic liver cirrhosis. Hepatogastroenterology 42(1), 22–26 (1995). Pyruvate dehydrogenase E1 deficiency is associated with Leigh syndrome, microcephaly, and motor neuropathy. Apolipoprotein B100 is involved in atherosclerosis and hypercholesterolemia. Hepatocyte growth factor (gf) is involved in stimulation of the growth of hepatocytes. Insulin-like growth factor-binding protein (IGFBP-3) predisposes breast cancer cells to programmed cell death. Ubiquitin is involved in dendrite outgrowth and differentiation. Cytochrome P450 2E1 is the principal catalyst of human oxidative halothane metabolism in vitro. (J Pharmacol Exp Ther 281(1), 400–411 (1997)). Thymosin beta-10 is detected mainly in malignant breast tissue, particularly in the cancerous cells, whereas the normal cell population around the lesions shows very weak staining. Also, the intensity of staining in the cancerous cells was proportionally increased with the increasing grade of the lesions. (Br J Cancer 1996 November; 74(9):1441–1444). In addition, in the highly metastatic human melanoma cell line, BLM, thymosin beta-10 correlated with the malignant phenotype. (Biochem Biophys Res Commun 1996 August 23;225(3): 808–816.)

The protein product of the gene can be assayed to determine the amount of expression. Methods for assaying for a protein include Western blot, immunprecipitation, radioimmunoassay. However, it is preferred according to the invention that the mRNA be assayed as an indication of expression. Methods for assaying for mRNA include Northern blots, slot blots, dot blots, and hybridization to an ordered array of oligonucleotides. Any method for specifically and quantitatively measuring a specific protein or mRNA or DNA product can be used.

Oligonucleotide probes for interrogating the tissue or cell sample are preferably of sufficient length to specifically hybridize only to appropriate, complementary genes or transcripts. Typically the oligonucleotide probes will be at least 10, 12, 14, 16, 18, 20 or 25 nucleotides in length. In some cases longer probes of at least 30, 40, or 50 nucleotides will be desirable.

The above disclosure generally describes the present invention. A more complete understanding can be obtained by reference to the following specific examples which are provided herein for purposes of illustration only, and are not intended to limit the scope of the invention.

EXAMPLE 1

Gee expression levels were quantitatively measured in human poly(A)+ and cDNA libraries using high density oligonucleotide arrays containing probes for more than 6500 human genes. Probe arrays (DNA chips) of this type have been shown to behave quantitatively with high specificity and sensitivity (Lockhart, D. J. et al., 1996, Nat. Biotech. 14:1657–1680). The arrays were designed and synthesized based on sequence information obtained from GenBank and dbEST. Half the genes were selected from full-length human sequences in Gen Bank and the remaining half were selected from clustered ESTs that have sequence similarity to genes of known function. Samples derived from adult brain, adult liver, fetal brain and fetal liver were hybridized to the probe arrays and the relative concentration of more than 6500 human genes were measured simultaneously. The RNAs were classified by relative abundance and differentially expressed genes were identified by direct comparison. The following comparisons were made; 1) fetal brain:adult brain, 2) fetal liver:adult liver, 3) adult brain:adult liver, 4) fetal brain:fetal liver. Using this method one can produce, in a relatively short period of time, a quantitative representation of gene expression for the major organs of the human body.

EXAMPLE 2

The sources of the samples interrogated are shown in Table 1. The samples were obtained commercially.

TABLE 1

Starting Material

| TISSUE | SOURCE | DESCRIPTION | CAT. # |
|---|---|---|---|
| Human Brain | | | |
| Fetal | cDNA | F & M, 19–23 wks | Str 937226 |
| Fetal | PolyA | F & M, 20–25 wks | CI 6525-1 |
| Adult | PolyA | F & M, 37–60 yrs | CI 6516-1 |
| Human Liver | | | |
| Adult | cDNA | M, 49 yrs | Str 937224 |
| Adolescent Liver | PolyA | F, 15 yrs | CI 6510-1 |
| Fetal | PolyA | F & M, 16–32 wks | CI 6527-1 |

EXAMPLE 3

The profiles using cloned brain cDNA and brain poly(A)$^+$ mRNA (reverse transcribed) as samples were compared. As shown in Table 2, each sample type yielded a large number of low copy messages. The percentage of the unique messages which were low copy messages was about the same for each sample source.

As shown in FIG. 1, a plot of the fetal brain hybridization intensities, poly(A)$^+$ versus cDNA yielded a line with a slope of 1.

TABLE 2 cDNA and Poly(A) Brain Message Comparison

| | cDNA - Poly(A) |
|---|---|
| Common | 1854 |
| Unique (cDNA) | 680 |
| Low copy | 500 (0.74) |
| Unique (polyA) | 329 |
| Low copy | 239 (0.73) |

EXAMPLE 4

The mRNA in brain and liver were compared (via their cDNA). Table 3 shows the results. The first column of data compares fetal brain and fetal liver. The second column of data compares fetal brain and adult brain. The third column of data compares the adolescent liver with the fetal liver. The percentage of low copy messages in fetal liver is very low. This indicates that the public databases (from which the probes were derived) contain an under representation of messages from fetal liver.

TABLE 3

Common and Unique mRNA in Brain and Liver

| | $FB_A - FL_B$ (%) | $FB_A - AB_B$ (%) | $AdL_A - FL_B$ (%) |
|---|---|---|---|
| Common (A + B) | 1176 | 1244 | 1268 |
| Unique (A) | 1035 | 941 | 547 |
| Low copy (A) | 691 (0.67) | 706 (0.75) | 279 (0.51) |
| Unique (B) | 651 | 159 | 534 |
| Low copy (V) | 51 (0.08) | 82 (0.52) | 157 (0.29) |

EXAMPLE 5

The results of the comparison of expression levels for 16 particular genes in fetal and adult, lung and brain, are shown in Table 4.

TABLE 4

| Accession number | Gene name | Intensity Abrain | Intensity Fbrain | Intensity Aliver | Intensity Fliver | |
|---|---|---|---|---|---|---|
| M12996 | G6PD | 210 | 180 | 70 | 0 | G6PD |
| T53360 | calcium channel | 490 | 350 | 0 | 0 | CACH |
| M55047 | synaptotagamin | 1380 | 430 | 0 | 0 | SYNTGN |
| M25667 | neuromodulin | 1500 | 2860 | 0 | 0 | NEUM |
| J04046 | calmodulin | 1500 | 1510 | 0 | 1970 | CAM |
| X53179 | nicotinic acetylcholine receptor beta 2 | 1430 | 0 | 0 | 0 | NACB2 |
| D16532 | VLDLR | 0 | 0 | 1300 | 0 | VLDLR |
| M64108 | udulin 1/undulin/excellmatr glycopro | 0 | 0 | 490 | 0 | XCMG/UN |
| T65758 | pyruvate dehydrogenase E1 | 230 | 230 | 5400 | 2290 | PYDHE1 |
| M10373 | apolipoprotein B100 | 0 | 0 | 8520 | 22850 | APOB100 |
| R85613 | hepatocyte gf | 0 | 0 | 400 | 3790 | HPGF |
| M74587 | IGF binding pro1 | 0 | 0 | 570 | 29520 | IGFBP1 |
| T88723 | ubiquitin | 6900 | 0 | 300 | 42490 | UBQ |
| R71212 | bone morphogenetic pro precursor | 10800 | 5560 | 0 | 0 | BMPP |
| H46990 | cytochrome p450-2E1 | 0 | 0 | 10510 | 0 | CYP2E1 |
| T63133 | thymosin beta-10 | 550 | 3840 | 2420 | 0 | THYB10 |

We claim:

1. A method of screening a drug for deleterious side effects on a cell comprising the steps of:
    assaying for the amount of expression in the cell of two or more genes selected from the group consisting of: G6PD, calcium channel, synaptotagamin, neuromodulin, calmodulin, nicotinic acetylcholine receptor beta 2, VLDLR, udulin1/undulin/extracellular matrix glycoprotein, pyruvate dehydrogenase E1, apolipoprotein B100, hepatocyte gf, IGF binding protein 1, ubiquitin, bone morphogenetic protein precursor, cytochrome p450-2E1, and thymosin beta-10, wherein the expression in the cell is assayed before and after the cell has been contacted with the drug, wherein alteration of the amount of expression of at least one of these genes by the drug is indicative of a deleterious side effect.

2. A method of distinguishing between a fetal and an adult liver sample comprising the steps of:

assaying for expression in the sample of two or more genes selected from the group consisting of: G6PD, calmodulin, VLDLR, udulin1/undulin/extracellular matrix glycoprotein, hepatocyte gf, IGF binding protein 1, ubiquitin, cytochrome p450-2E1, and thymosin beta-10, wherein expression of G6PD, VLDLR, udulin1/undulin/extracellular matrix glycoprotein, cytochrome p450-2E1, and thymosin beta-10 are indicative of an adult liver, and expression of calmodulin, hepatocyte gf IGF binding protein 1, and ubiquitin are indicative of a fetal liver.

3. A method of distinguishing between a fetal and adult brain tissue, comprising the steps of:

assaying for expression in the tissue of two or more genes selected from the group consisting of: nicotinic acetylcholine receptor beta 2, ubiquitin, and thymosin beta-10, wherein expression of nicotinic acetylcholine receptor beta 2 or ubiquitin indicates an adult brain.

4. A method of determining the source of a tissue as adult brain or adult liver, comprising the steps of:

assaying for expression in the tissue of two or more genes selected from the group consisting of: calcium channel, synaptotagamin, neuromodulin, calmodulin, nicotinic acetylcholine receptor beta 2, VLDLR, udulin1/undulin/extracellular matrix glycoprotein, pyruvate dehydrogenase E1, apolipoprotein B100, hepatocyte gf, IGF binding protein 1, ubiquitin, bone morphogenetic protein precursor, and cytochrome p450-2E1, wherein expression of calcium channel, synaptotagamin, neuromodulin, calmodulin, nicotinic acetylcholine receptor beta 2, ubiquitin, or bone morphogenetic protein precursor indicates a brain source for the tissue, and wherein expression of pyruvate dehydrogenase E1, VLDLR, udulin1/undulin/extracellular matrix glycoprolein, apolipoprotein B100, thymosin beta-10, hepatocyte gf, IGF binding protein 1, or cytochrome p450-E1 indicates a liver source for the tissue.

5. A method of distinguishing a tissue source as fetal brain or fetal liver, comprising the steps of:

assaying for expression in the tissue of two or more genes selected from the group consisting; of: G6PD, calcium channel, synaptotagamin, neuromodulin, pyruvate dehydrogenase E1, apolipoprotein B100, hepatocyte gf, IGF binding protein 1, ubiquitin, bone morphogenetic protein precursor, and thymosin beta-10, wherein expression of G6PD, calcium channel, synaptotagamin, neuromodulin, thymosin beta-10 or bone morphogenetic protein precursor indicates a fetal brain source and expression of pyruvate dehydrogenase E1, apolipoprotein B100, hepatocyte gf, IGF binding protein 1, ubiquitin, indicates a fetal liver source.

6. The method of claim 1, 2, 3, 4, or 5, wherein expression of at least 3 genes are assayed.

7. The method of claim 1, 2, 4, or 5, wherein expression of at least 4 genes are assayed.

8. The method of claim 1, 2, 4, or 5, wherein expression of at least 5 genes are assayed.

9. The method of claim 1, 2, 4, or 5, wherein expression of at least 6 genes are assayed.

10. The method of claim 1, 2, 4, or 5, wherein expression of at least 7 genes are assayed.

11. The method of claim 1, 2, 4, or 5, wherein expression of at least 8 genes are assayed.

12. The method of claim 1, 2, 4, or 5, wherein expression of at least 9 genes are assayed.

13. The method of claim 1, 4, or 5, wherein expression of at least 10 genes are assayed.

14. A solid support for screening a drug for deleterious side effects on a cell comprising: at least two oligonucleotides for probing two or more genes selected from the group consisting of: G6PD, calcium channel, synaptotagamin, neuromodulin, calmodulin, nicotinic acetylcholine receptor beta 2, VLDLR, udulin1/undulin/extracellular matrix glycoprotein, pyruvate dehydrogenase E1, apolipoprotein B100, hepatocyte gf, IGF binding protein 1, ubiquitin, bone morphogenetic protein precursor, cytochrome p450-2E1, and thymosin beta-10, wherein each oligonucleotide comprises a sequence which is complementary to one of the two or more genes.

15. A solid support for distinguishing between a fetal and an adult liver sample comprising: two or more oligonucleotides for detecting two or more genes selected from the group consisting of: G6PD, calmodulin, VLDLR, udulin1/undulin/extracellular matrix glycoprotein, hepatocyte gf, IGF binding protein 1, ubiquitin, cytochrome p450-2E1, and thymosin beta-10 wherein each oligonucleotide comprises a sequence which is complementary to one of the two or more genes.

16. A solid support for distinguishing between a fetal and adult brain tissue, comprising: two more oligonucleotides for detecting two or more genes selected from the group consisting of: nicotinic acetylcholine receptor beta 2, ubiquitin, and thymosin beta-10, wherein each oligonucleotide comprises a sequence which is complementary to one of the two or more genes.

17. A solid support for determining the source of a tissue as adult brain or adult liver, comprising:

two or more oligonucleotides for detecting two or more genes selected from the group consisting of: calcium channel, synaptotagamin, neuromodulin, calmodulin, nicotinic acetylcholine receptor beta 2, VLDLR, udulin1/undulin/extracellular matrix glycoprotein, pyruvate dehydrogenase E1, apolipoprotein B100, hepatocyte gf, IGF binding protein 1, ubiquitin, bone morphogenetic protein precursor, and cytochrome p450-2E1, wherein each oligonucleotide comprises a sequence which is complementary to one of the two or more genes.

18. A solid support for distinguishing a tissue source as fetal brain or fetal liver, comprising: two or more oligonucleotides for detecting two or more genes selected from the group consisting of: G6PD, calcium channel, synaptotagamin, neuromodulin, pyruvate dehydrogenase E1, apolipoprotein B100, hepatocyte gf, IGF binding protein 1, ubiquitin, bone morphogenetic protein precursor, and thymosin beta-10, wherein each oligonucleotide comprises a sequence which is complementary to one of the two or more genes.

19. The solid support of claim 14, 15, 16, 17, or 18 which is an array comprising at least 10 different oligonucleotides in discrete locations per $cm^2$.

20. The solid support of claim 14, 15, 16, 17, or 18 which is an array comprising at least 100 different oligonucleotides in discrete locations per $cm^2$.

21. The solid support of claim 14, 15, 16, 17, or 18 which is an array comprising at least 1,000 different oligonucleotides in discrete locations per $cm^2$.

22. The solid support of claim 14, 15, 16, 17, or 18 which is an array comprising at least 10,000 different oligonucleotides in discrete locations per $cm^2$.

* * * * *